US008210852B2

(12) United States Patent
Miller et al.

(10) Patent No.: US 8,210,852 B2
(45) Date of Patent: Jul. 3, 2012

(54) ARTIFICIAL BONES AND METHODS OF MAKING SAME

(75) Inventors: Forrest A. Miller, Vashon, WA (US); Amy E. Johnson, Seattle, WA (US)

(73) Assignee: Pacific Research Laboratories, Inc., Vashon, WA (US)

( * ) Notice: Subject to any disclaimer, the term of this patent is extended or adjusted under 35 U.S.C. 154(b) by 590 days.

(21) Appl. No.: 12/101,853

(22) Filed: Apr. 11, 2008

(65) Prior Publication Data
US 2009/0216327 A1    Aug. 27, 2009

Related U.S. Application Data

(60) Provisional application No. 60/917,601, filed on May 11, 2007, provisional application No. 60/911,270, filed on Apr. 11, 2007.

(51) Int. Cl.
*G09B 23/28* (2006.01)
(52) U.S. Cl. ........................................................ 434/274
(58) Field of Classification Search .................. 434/262, 434/267, 274; 623/23.56, 23.58
See application file for complete search history.

(56) References Cited

U.S. PATENT DOCUMENTS

| | | | | |
|---|---|---|---|---|
| 4,106,219 | A * | 8/1978 | Schneider et al. | 434/274 |
| 4,629,464 | A * | 12/1986 | Takata et al. | 623/23.61 |
| 6,471,519 | B1 * | 10/2002 | Biermann et al. | 434/274 |
| 6,932,610 | B2 * | 8/2005 | Ono et al. | 434/274 |
| 6,977,095 | B1 * | 12/2005 | Marx et al. | 427/2.26 |
| 7,018,212 | B2 * | 3/2006 | Zeeff | 434/274 |
| 7,052,518 | B2 * | 5/2006 | Irie et al. | 623/23.56 |
| 7,699,615 | B2 * | 4/2010 | Sakezles | 434/274 |
| 7,758,792 | B2 * | 7/2010 | Yamazawa et al. | 264/308 |
| 7,772,146 | B2 * | 8/2010 | McGowan | 501/123 |
| 2005/0049715 | A1 * | 3/2005 | Ito et al. | 623/23.5 |
| 2008/0133026 | A1 * | 6/2008 | Lei et al. | 623/23.54 |

OTHER PUBLICATIONS

Chou, K.-S., and M.-A. Song, "A Novel Method for Making Open-Cell Aluminum Foams With Soft Ceramic Balls," Scripta Materialia 46(5):379-382, Mar. 2002.
Cvijanovic, O., et al., "Age- and Region-Dependent Changes in Human Lumbar Vertebral Bone: A Histomorphometric Study," SPINE 29(21):2370-2375, Nov. 2004.
Gibson, L.J., "The Mechanical Behaviour of Cancellous Bone," Journal of Biomechanics 18(5):317-328, 1985.
Goldstein, S.A., et al., "The Mechanical Properties of Human Tibial Trabecular Bone as a Function of Metaphyseal Location," Journal of Biomechanics 16(12):965-969, 1983.
Haddock, S.M., et al., "Similarity in the Fatigue Behavior of Trabecular Bone Across Site and Species," Journal of Biomechanics 37(2):181-187, Feb. 2004.
Hernandez, C.J., and T.M. Keaveny, "A Biomechanical Perspective on Bone Quality," Bone 39(6):1173-1181, Dec. 2006.
Johnson, A.E., and T.S. Keller, "Mechanical Properties of Open-Cell Foam Synthetic Thoracic Vertebrae," Journal of Materials Science: Materials in Medicine 19(3):1317-1323, Sep. 2007.

(Continued)

*Primary Examiner* — Kurt Fernstrom
(74) *Attorney, Agent, or Firm* — Christensen O'Connor Johnson Kindness PLLC

(57) ABSTRACT

An artificial bone generally includes an outer wall defining an inner cavity and an inner core disposed within at least a portion of the inner cavity, wherein the inner core includes a porous material having stiffness within a range of stiffness properties for mammalian cancellous bone and strength within a range of strength properties for mammalian cancellous bone.

13 Claims, 9 Drawing Sheets

OTHER PUBLICATIONS

Keaveny, T.M., et al., "Trabecular Bone Modulus and Strength Can Depend on Specimen Geometry," Journal of Biomechanics 26(8):991-1000, 1993.

Keller, T.S., "Predicting the Compressive Mechanical Behavior of Bone," Journal of Biomechanics 27(9):1159-1168, Sep. 1994.

Kopperdahl, D.L., et al., "Quantitative Computed Tomography Estimates of the Mechanical Properties of Human Vertebral Trabecular Bone," Journal of Orthopaedic Research 20(4):801-805, Jul. 2002.

Kopperdahl, D.L., and T.M. Keaveny, "Yield Strain Behavior of Trabecular Bone," Journal of Biomechanics 31(7):601-608, Jul. 1998.

Morgan, E.F., et al., "Trabecular Bone Modulus-Density Relationships Depend on Anatomic Site," Journal of Biomechanics 36(7):897-904, Jul. 2003.

Palissery, V., et al., "Fatigue Characterization of a Polymer Foam to Use as a Cancellous Bone Analog Material in the Assessment of Orthopaedic Devices," Journal of Materials Science: Materials in Medicine 15(1):61-67, Jan. 2004.

Parkinson, I.H., and N.L. Fazzalari, "Interrelationships Between Structural Parameters of Cancellous Bone Reveal Accelerated Structural Change at Low Bone Volume," Journal of Bone and Mineral Research 18(12):2200-2205, Nov. 2003.

Pattin, C.A., et al., "Cyclic Mechanical Property Degradation During Fatigue Loading of Cortical Bone," Journal of Biomechanics 29(1):69-79, Jan. 1996.

Rapillard, L., et al., "Compressive Fatigue Behavior of Human Vertebral Trabecular Bone," Journal of Biomechanics 39(11):2133-2139, 2006.

Wixson, R.L., et al., "Cancellous Bone Material Properties in Osteoarthritic and Rheumatoid Total Knee Patients," Journal of Orthopaedic Research 7(6):885-892, 1989.

Zhu, M., et al., "Effects of Specimen Load-Bearing and Free Surface Layers on the Compressive Mechanical Properties of Cellular Materials," Journal of Biomechanics 27(1):57-66, Jan. 1994.

Bowman, S.M., et al., "Creep Contributes to the Fatigue Behavior of Bovine Trabecular Bone," Journal of Biomechanical Engineering 120(5):647-654, Oct. 1998.

Pacific Research Laboratories, Inc., Vashon Island, Wash., Invoice No. 108612, billed to Synthes, Ltd. (USA), Paoli, Penn., dated May 16, 2006, in response to Sales Order No. 73270, dated Mar. 27, 2006, 4 pages.

* cited by examiner

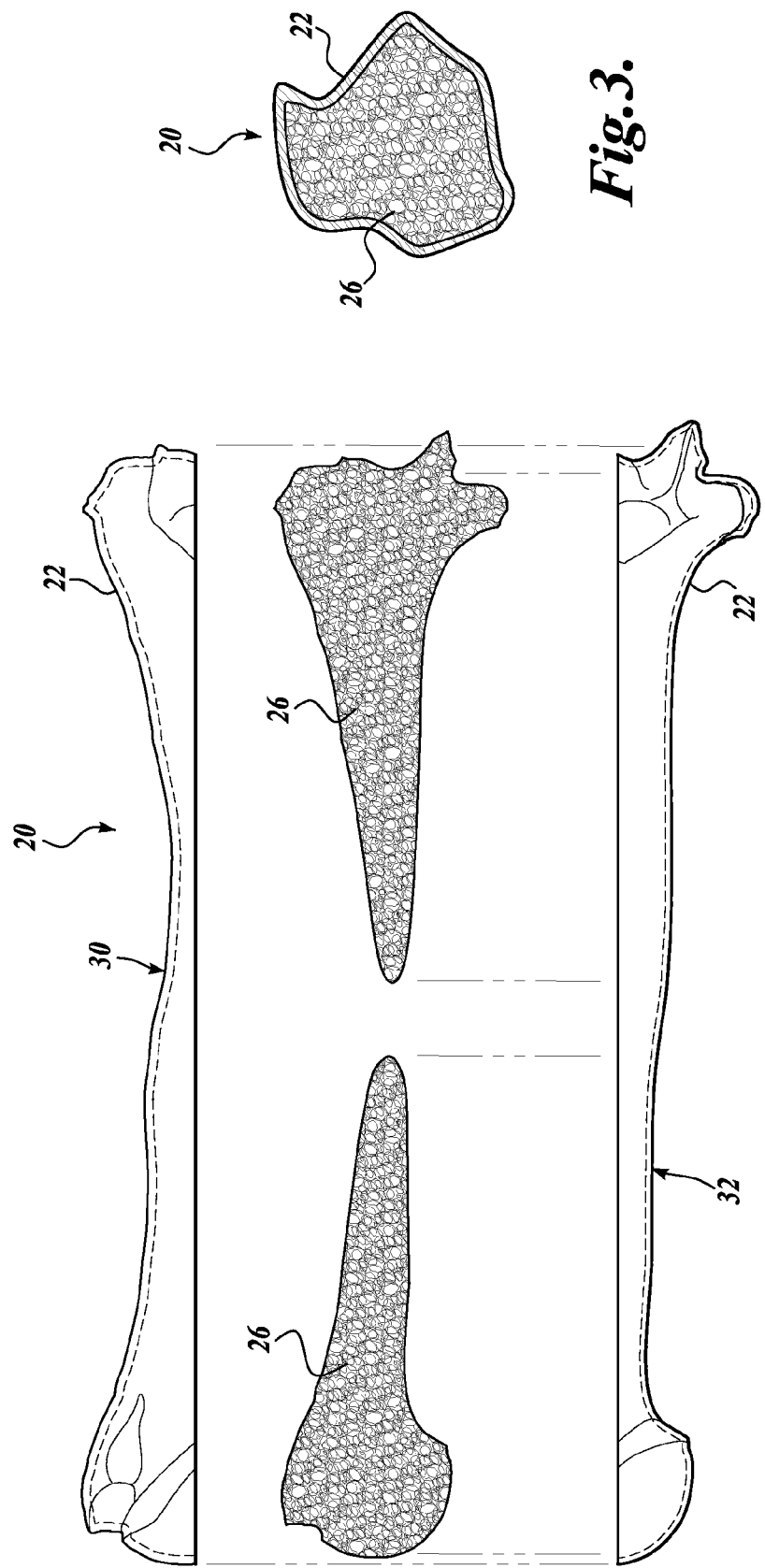

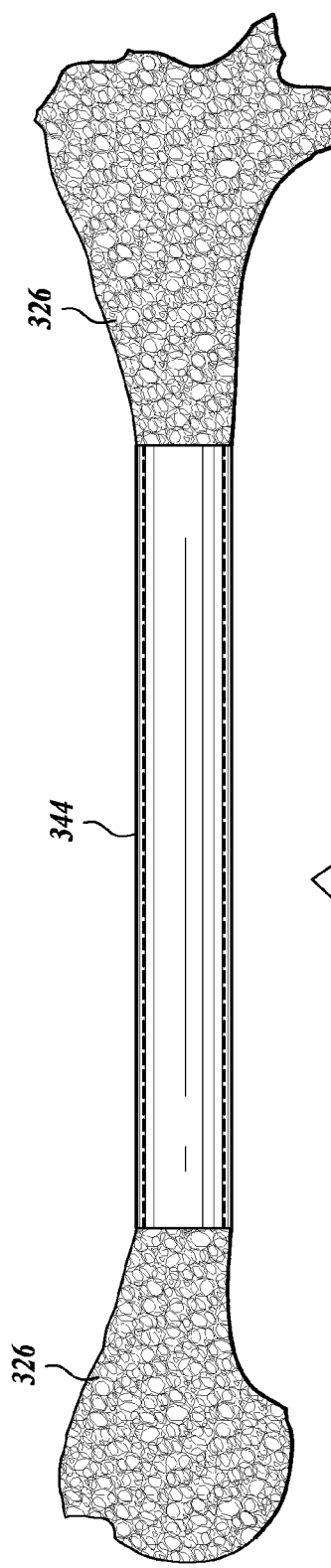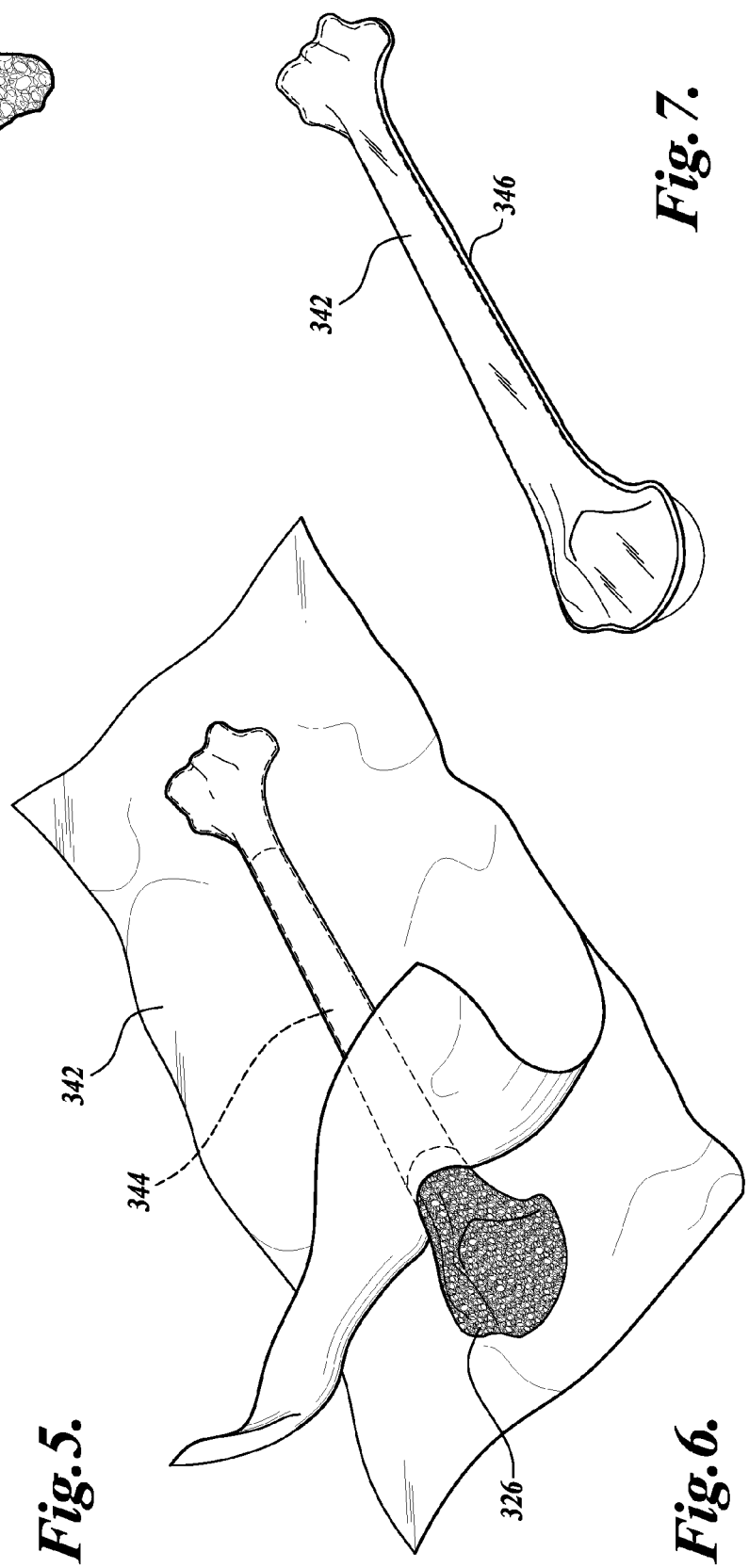
Fig. 5.
Fig. 6.
Fig. 7.

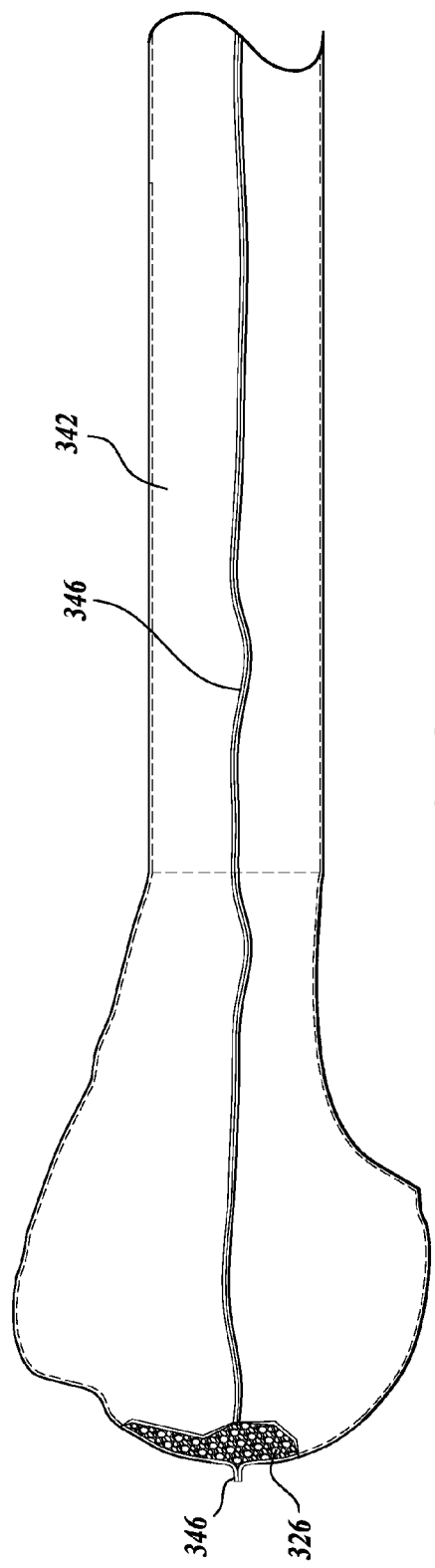
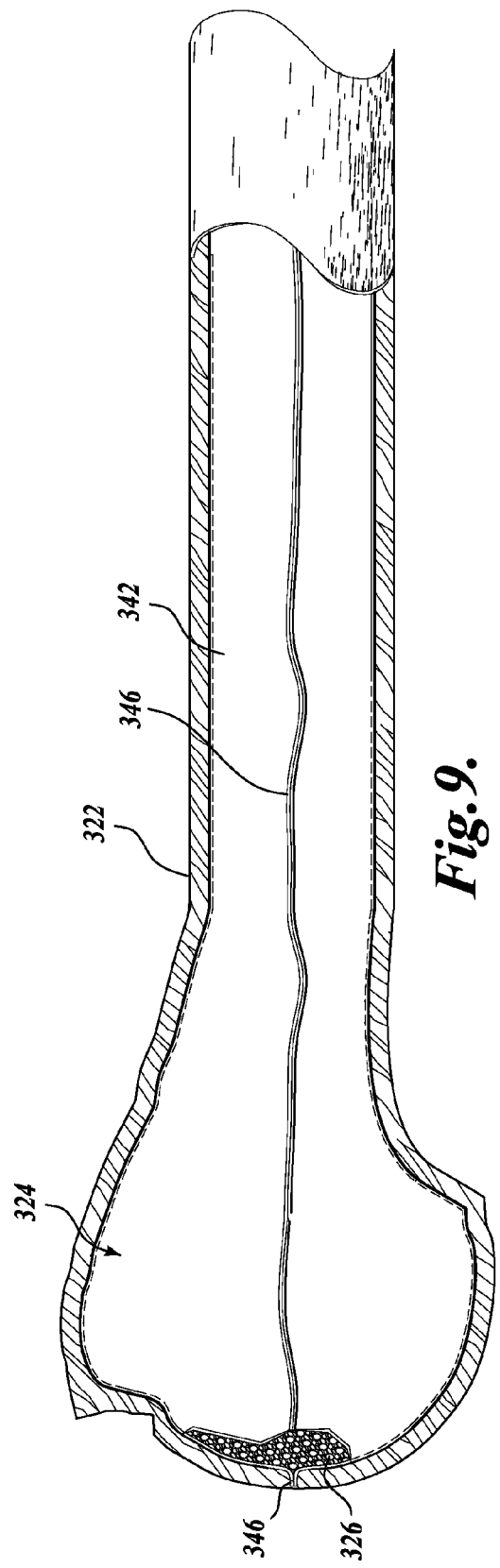

ARTIFICIAL BONES AND METHODS OF MAKING SAME

CROSS-REFERENCES TO RELATED APPLICATIONS

This application claims the benefit of U.S. Provisional Application No. 60/917,601, filed May 11, 2007, and U.S. Provisional Application No. 60/911,270, filed Apr. 11, 2007, the disclosures of which are hereby expressly incorporated by reference.

TECHNICAL FIELD

Embodiments of the present disclosure relate generally to artificial bones for use in orthopedic instruction and methods of making the same.

BACKGROUND

In orthopedic surgery, bone and joint cutting or drilling is a preliminary step before the insertion of orthopedic hardware (such as pins or screws) into bones or joints during the repair of a bone fracture or installation of a prosthetic device. Accordingly, orthopedic surgeons require bone cutting and drilling skills. These skills are obtained by practicing on bones and joints from cadavers, which are very expensive and in short supply, or on artificial bones manufactured for such practice.

In some instances, surgeons must perform more extensive procedures beyond cutting and/or drilling into the bone to set orthopedic hardware in the bones or joints. For example, after drilling a hole in the bone or joint, the surgeon might administer a bone structure reinforcement compound, such as a bone cement compound, through a percutaneous or injection method into the bone or joint. The bone cement penetrates the cancellous bone area. A pin or screw may then be inserted into the hole, and the bone cement hardens therearound to set the pin or screw within the reinforced bone. The penetration of the bone cement through an artificial cancellous bone area is limited in current artificial bones because currently designed artificial bones typically include a closed cell artificial cancellous bone area having no interstices or passages between cells for the bone cement to travel through. Moreover, these currently designed artificial bones do not have characteristics and properties that correspond to other characteristics and properties of mammalian bones.

Therefore, there exists a need for improved artificial bones and joints that perform like mammalian bone when subjected to the procedures designed for fracturing and repairing such bones, for augmenting the bone structure with reinforcing compounds, such as bone cements, and for other static and dynamic biomechanical experimentation.

Moreover, current artificial bones are typically manufactured by reaction injection molding a lower density polyurethane closed cell artificial cancellous bone on a pin or mandrel in a first mold, then molding a higher density polyurethane artificial cortical bone around the artificial cancellous bone in a second larger mold, then removing the pin or mandrel. Because an open cell artificial cancellous bone cannot be reaction injection molded using the same method used for a closed cell artificial cancellous bone, there also exists a need for improved methods of making improved artificial bones and joints using open cell artificial cancellous bone.

SUMMARY

This summary is provided to introduce a selection of concepts in a simplified form that are further described below in the detailed description. This summary is not intended to identify key features or essential features of the claimed subject matter, not is it intended to be used to limit the scope of the claimed subject matter.

In accordance with one embodiment of the present disclosure, an artificial bone is provided. The artificial bone generally includes an outer wall defining an inner cavity and an inner core disposed within at least a portion of the inner cavity, wherein the inner core includes a porous material having stiffness within a range of stiffness properties for mammalian cancellous bone and strength within a range of strength properties for mammalian cancellous bone, wherein the inner core includes a barrier layer to separate the outer wall from the porous material.

In accordance with another embodiment of the present disclosure, an artificial bone is provided. The artificial bone generally includes an outer wall defining an inner cavity; and an inner core disposed within at least a portion of the inner cavity, wherein the inner core comprises a porous material having an apparent modulus of elasticity of at least about 26 MPa and ultimate stress of at least about 0.32 MPa.

In accordance with another embodiment of the present disclosure, a method of making an artificial bone is provided. The method generally includes obtaining an inner core, wherein the inner core includes a porous material having stiffness within a range of stiffness properties for mammalian cancellous bone and strength within a range of strength properties for mammalian cancellous bone; substantially covering the inner core with a barrier layer; and molding a substantially continuous outer wall around the inner core.

In accordance with another embodiment of the present disclosure, a method of making an artificial bone is provided. The method generally includes obtaining first and second outer wall portions, wherein each of the first and second outer wall portions define a portion of an inner cavity such that when the first and second outer wall portions are assembled into an outer wall, the outer wall defines an inner cavity; obtaining a hardened inner core configured to fit within at least a portion of the inner cavity; inserting the inner core within at least a portion of the inner cavity of the first outer wall portion; and attaching the second outer wall portion to the first outer wall portion to form the outer wall having the inner core disposed within the at least a portion of the inner cavity.

In accordance with another embodiment of the present disclosure, a method of making an artificial bone is provided. The method generally includes obtaining an outer wall portion, wherein the outer wall portion defines at least a portion of an inner cavity; obtaining an inner core configured to fit within at least a portion of the inner cavity, wherein the inner core comprises a formable porous material; inserting the inner core within at least a portion of the inner cavity of the first outer wall portion; and hardening the inner core after inserting the inner core within the at least a portion of the inner cavity of the outer wall portion.

DESCRIPTION OF THE DRAWINGS

The foregoing aspects and many of the attendant advantages of this disclosure will be more readily understood by reference to the following detailed description, when taken in conjunction with the accompanying drawings, wherein:

FIG. 2 is an exploded view of the artificial bone of FIG. 1;

FIG. 3 is a cross-sectional view of the artificial bone taken through the plane 3-3 of FIG. 1;

FIGS. 5-9 show a method according to various aspects of the present disclosure of making an artificial bone having an open cell artificial cancellous bone and a substantially continuous artificial cortical bone;

DETAILED DESCRIPTION

Embodiments of the present disclosure are generally directed to artificial bones and methods of making these bones. An artificial bone 20 constructed in accordance with one embodiment of the present disclosure may be best understood by referring to FIG. 1. The bone 20 includes an outer wall 22 having an inner cavity 24, and an inner core 26 disposed within at least a portion of the inner cavity 24. As described in greater detail below, the outer wall 22 and the inner cavity 24 are designed and configured to have characteristics and properties that are similar to mammalian bone when subjected to the procedures designed for fracturing and repairing bones, including bones and bone joints, and when subjected to dynamic biomechanical experimentation.

The artificial bone 20 is a manufactured alternative to mammalian cadaver bones for use in orthopedic instruction and experimentation. Accordingly, the artificial bone 20 is designed to simulate mammalian bone when broken and subjected to repair, for example, when subjected to cutting, drilling, and/or the injection of bone structure reinforcing compounds, such as bone cement compounds. In addition, the artificial bone 20 offers an alternative to human bones for examining the effectiveness of cementitious compounds to be used in bone repair procedures or in cement augmentation for osteoporotic bones. Further, the artificial bone 20 offers an alternative to human bones for static and dynamic biomechanical experiments. For example, artificial bones can be used to test the life cycle and durability of prostheses, artificial joints, orthopedic hardware and devices, etc. Under the conditions described above, artificial bones are a preferable alternative to cadaver bones because they have reduced inter-specimen variation, do not degrade over time, and are generally lower in cost in comparison to cadaver bones.

Figure 1:
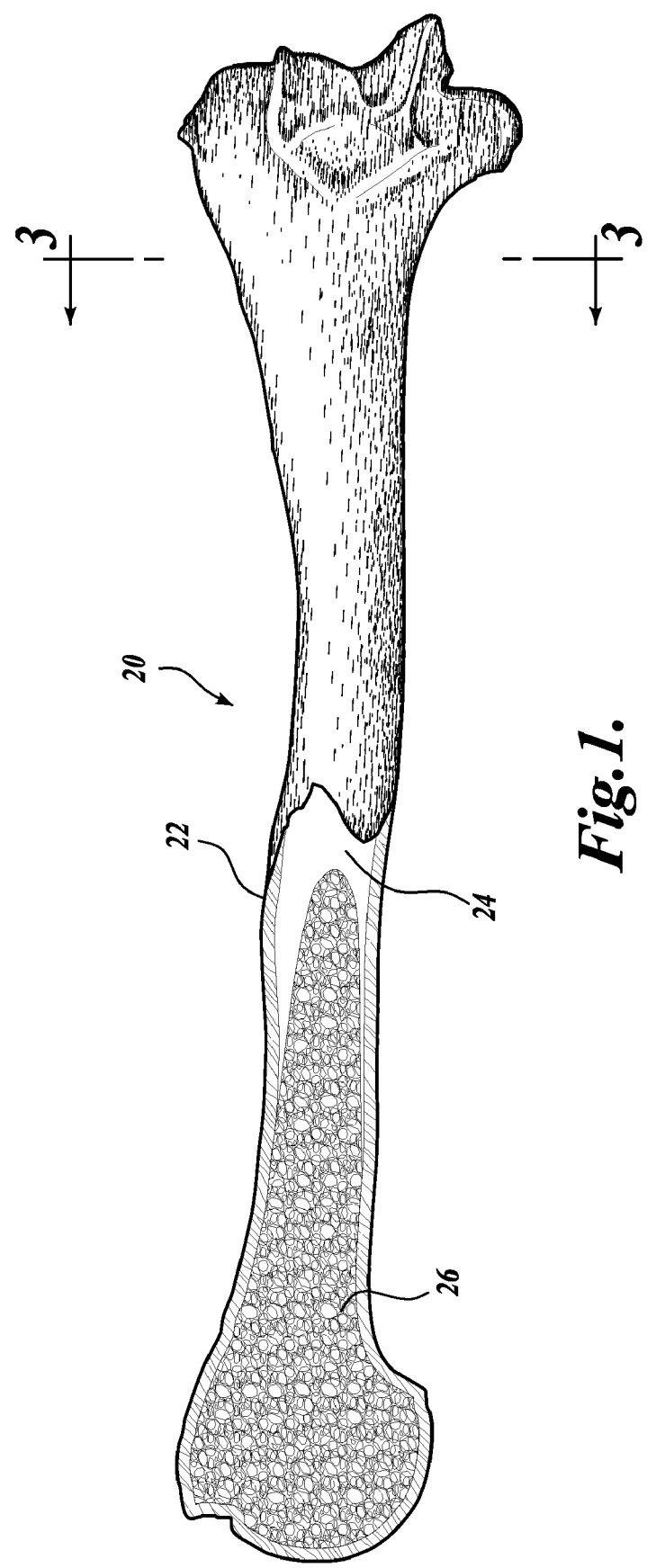
FIG. 1 is a partial cut-away view of an artificial bone formed according to various aspects of the present disclosure.

In the illustrated embodiment of FIGS. 1-3, there is shown an artificial human humerus bone 20; however, it should be understood that all mammalian bones and joints, in addition to the human humerus bone, are within the scope of the present disclosure. The properties of the outer wall 22, inner cavity 24, and inner core 26 of the artificial bone 20 are all designed to have characteristics and features similar to mammalian cortical bone, medullar cavity, and cancellous bone, as will now be described in greater detail. Depending on the type of bone, such characteristics and features may include standard morphological properties of mammalian bone, such as volume fraction, surface to volume ratio, trabecular number, trabecular thickness, trabecular spacing or cell size, intercept length, connectivity index, degree of anisotropy, and characterization of the bone. In addition, such characteristics and features may include compressive properties of mammalian bone, such as apparent density, stiffness, measured as apparent modulus of elasticity, and strength, measured as ultimate stress.

The outer wall 22 is designed and configured to have characteristics and features similar to mammalian cortical bone when subjected to the procedures designed for fracturing and repairing bones and joints and when subjected to biomechanical experimentation. In that regard, the outer wall 22 may be made from a rigid, fracturable and drillable material, such as a rigid polymer material. Suitable materials include, but are not limited to, thermoplastics and thermosets, such as polyurethanes, resins, fiberglass, fiberglass filled resins and epoxies, and other suitable materials. In one embodiment, the outer wall 22 is reaction injection molded from a liquid polyurethane foam that is transferred to a mold for the outer wall. The thickness of the outer wall 22 may also be designed and configured to simulate mammalian bone. In that regard, a thicker outer wall 22 is generally used to simulate healthy mammalian bones, while a thinner outer wall 22 is generally used to simulate osteoporotic mammalian bones. The thickness of an artificial osteoporotic bone is generally about 50% to about 80% less than the thickness of an artificial healthy bone.

The inner cavity 24 is designed and configured to have characteristics and features similar to a mammalian medullar cavity when subjected to the procedures designed for fracturing and repairing bones and when subjected to biomechanical experimentation. In the illustrated embodiment, the inner cavity 24 is shown as an empty cavity. However, it should be understood that the inner cavity may include a spacer or bladder and/or may be filled with suitable materials for ease of manufacturing or for other design or functional factors.

As shown in FIGS. 1-3, the inner core 26 is disposed within at least a portion of the inner cavity 24. The inner core 26 is also designed and configured to have similar characteristics and features as mammalian cancellous bone (or trabecular bone) when subjected to the procedures designed for fracturing and repairing bones and when subjected to biomechanical experimentation. In that regard, the inner core 26 generally has a porous, open cell structure, including interstices or passages between cells. These interstices are designed to be permeable to high-viscosity fluids, such as air, water, and other fluids. Being permeable to fluids, the interstices are designed to be penetrated by a bone structure reinforcing compound, such as a bone cement compound, when the compound is injected or otherwise introduced into the region, for example, for the purposes of cement augmentation or setting orthopedic hardware and devices (including, but not limited to, pins, screws, wires, rods, anchors, prostheses, artificial joints, joint repair hardware, and other devices used to repair bones).

As seen in the illustrated embodiment of FIG. 9, the inner core 326 may include a barrier layer 342 to prevent outer wall 322 molding materials from penetrating the porous, open cell structure of the inner core 326 during manufacture, as described in greater detail below. The barrier layer 342 may be an plastic film layer that is impermeable to the molding materials of the outer wall 322 used to cover the outer surface of the inner core 326. As a non-limiting example, the barrier layer 324 may be a urethane film.

An inner core 26 formed in accordance with embodiments of the present disclosure has morphological properties that are similar to or within a range of properties for mammalian cancellous bone, such as volume fraction, surface to volume ratio, connectivity index, and characterization, as described in greater detail below in EXAMPLE 1. In addition, an inner core 26 formed in accordance with embodiments of the present disclosure has stiffness, strength, and density properties that are within the range of properties for mammalian cancellous bone when tested under compression. The range of compressive properties for mammalian cancellous bone were compiled from mean data for 1133 compressive test samples performed on either cylindrical cores or cube specimens of human cancellous bone taken from vertebrae, femurs, and tibias from cadaver bone aged 20-100 years, using a method with uniaxial compression loading at various strain rates. Large ranges and variations in the mechanical properties of human cancellous bone, as shown in TABLE 2 in EXAMPLE 2 below, may be a result of differences in subject age, degeneration, bone density, and source of bone (e.g., vertebral, tibial, etc.).

The human cancellous bone data was compiled from the following documents, the disclosures of which are hereby incorporated by reference:

Gibson, L. J., "The Mechanical Behavior of Cancellous Bone," J. Biomechanics 18(5):317-328, 1985;

Goldstein, S. A., et al. "The Mechanical Properties of Human Tibial Trabecular Bone As a Function of Metaphyseal Location," J. Biomechanics 16(12):965-969, 1983;

Keller, T. S., "Predicting the Compressive Mechanical Behaviour of Bone;" J. Biomechanics 27(9):1159-1168, 1994;

Kopperdahl, D. L., Keaveny, T. M., "Yield Strain Behavior of Trabecular Bone," J. Biomechanics 31:601-608, 1998; and Kopperdahl, D. L., et al. "Quantitative Computed Tomography Estimates of the Mechanical Properties of Human Vertebral Trabecular Bone," J. Orthop. Res. 20:801-805, 2002.

Additional sources of human cancellous bone data include the following documents, the disclosures of which are hereby incorporated by reference:

Morgan, E. F., Bayraktar, H. H., Keaveny, T. M., "Trabecular bone modulus-density relationships depend on anatomic site," J. Biomech. 36:897-904, 2003; and Hernandez, C. J., Keaveny, T. M., "A biomechanical perspective on bone quality," J. Biomech. 39:1173-1181, 2006.

While it should be appreciated that there are large ranges and variations in the mechanical properties of human cancellous bone, the inventors have found that certain ranges of stiffness, strength, and apparent density properties have characteristics and features similar to a mammalian medullar cavity when subjected to the procedures designed for fracturing and repairing bones and when subjected to biomechanical experimentation. In that regard, suitable ranges for these properties are shown in TABLE 2 in EXAMPLE 2 and described in greater detail below. The inventors have further found that stiffness and strength properties increase with increased apparent density. The inventors have further found that the upper limit for apparent density is defined by the openness of the interstices and passages between cells of the open cell structure required to allow for permeation of a bone structure reinforcing compound, such as a bone cement compound. If the apparent density of the open cell structure becomes too high, the cells are not open enough to allow penetration of a bone cement compound.

Regarding stiffness, in one embodiment of the present disclosure, the inner core 26 has an apparent modulus of elasticity of at least about 26 MPa. In another embodiment, the inner core 26 has an apparent modulus of elasticity in a range of about 26 MPa to about 673 MPa. In another embodiment, the inner core 26 has an apparent modulus of elasticity in a range of about 55 MPa to about 535 MPa. In another embodiment, the inner core 26 has an apparent modulus of elasticity in a range of about 26 MPa to about 200 MPa. In yet another embodiment, the inner core 26 has an apparent modulus of elasticity in a range of about 26 MPa to about 100 MPa.

Regarding strength, in one embodiment of the present disclosure, the inner core 26 has strength, measured as ultimate stress, of at least about 0.32 MPa. In another embodiment, the inner core 26 has ultimate stress in a range of about 0.32 MPa to about 46 MPa. In another embodiment, the inner core 26 has ultimate stress in a range of about 0.34 MPa to about 12.08 MPa. In another embodiment, the inner core 26 has ultimate stress in a range of about 0.32 MPa to about 1.0 MPa. In yet another embodiment, the inner core 26 has ultimate stress in a range of about 0.32 MPa to about 0.60 MPa.

Regarding apparent density, in one embodiment of the present disclosure, the inner core 26 has an apparent density of at least about 0.09 g/cm$^3$. In another embodiment, the inner core 26 has an apparent density in a range of about 0.09 g/cm$^3$ to about 0.64 g/cm$^3$. In another embodiment, the inner core 26 has an apparent density in a range of about 0.09 g/cm$^3$ to about 0.49 g/cm$^3$. In another embodiment, the inner core 26 has an apparent density in a range of about 0.12 g/cm$^3$ to about 0.49 g/cm$^3$. In yet another embodiment, the inner core 26 has an apparent density in a range of about 0.15 g/cm$^3$ to about 0.49 g/cm$^3$.

It should be appreciated that osteoporotic cancellous bone has lower stiffness and/or strength properties when tested under compression compared to healthier, non-osteoporotic bones. In that regard, osteoporotic cancellous bone generally has an apparent modulus of elasticity values of less than about 100 MPa and ultimate stress values of less than about 2 MPa, while healthier, non-osteoporotic cancellous bone generally has an apparent modulus of elasticity values of greater than about 100 MPa and ultimate stress values of greater than about 2 MPa.

Likewise, osteoporotic cancellous bone generally has a lower apparent density compared to healthier, non-osteoporotic cancellous bone. In that regard, osteoporotic cancellous bone generally has an apparent density of less than about 0.20 g/cm$^3$, while healthier, non-osteoporotic cancellous bone generally has an apparent density of greater than about 0.20 g/cm$^3$. In accordance with these properties, inner cores formed in accordance with the foregoing embodiments (including inner cores that simulate both osteoporotic and healthy mammalian cancellous bone) may show some crumbling when subjected to fracturing, cutting, drilling, or the insertion of hardware, such as pins and/or screws, similar to the properties of mammalian cancellous bone subjected to the same procedures.

In one embodiment of the present disclosure, an inner core 26 that has properties and characteristics corresponding to mammalian cancellous bone, as described above, is a hardened reticulated open cell foam. In that regard, the inner core 26 is a dry, formable, reticulated open cell foam, such as an open cell polyurethane, polyester, or other suitable open cell foam, for example, polyurethane open cell foam having about 14 ppi (pores per inch) and being about 95% open, manufactured by the E.N. MURRAY CO. and sold as product PTA 14 ppi Natural, having a density of about 0.023 g/cm$^3$. In other embodiments, the open cell foam has pores per inch in the range of about 10 to about 45 pores per inch.

The reticulated open cell foam begins as a formable or pliable foam, but is impregnated with an inner core hardening agent, such as resin, ceramic, or metal, including alloys or oxides thereof, to fabricate suitable strength, stiffness, and density properties for the foam to simulate mammalian cancellous bone, as described in greater detail above. Such impregnation of the foam may be accomplished by dipping, saturating, coating, or injecting the inner core hardening agent, or by any other method of impregnation by a fluid hardening agent. As the impregnated hardening agent cures within the foam open cell structure, the once-formable foam becomes a hardened foam having strength, stiffness, and density properties in accordance with the present disclosure. A suitable amount of hardening agent applied to the open cell foam achieves stiffness, strength, and apparent density properties that are similar to or within a range of properties for mammalian cancellous bone, while also maintaining a suitable open cell structure to allow a bone structure reinforcing compound, such as bone cement, to penetrate through the open cells.

In a preferred embodiment, the formable open cell foam is impregnated with epoxy, urethane, silicon, ceramic, or other suitable hardening resins. As nonlimiting examples, suitable epoxy resins include, but are not limited to, marine grade epoxy resin, manufactured by TAP®, including resin #314 blended with B-side hardener #109, RENLAM®4017 resin blended with Ren®1510 hardener manufactured by HUNTSMAN™, and epoxy resin systems manufactured by COTRONICS CORPORATION.

The resin can be suitably combined with filler materials to increase the strength properties of the hardened open cell foam. Suitable filler materials include, but are not limited to, glass fiber, such as 3032 milled e-glass fiber, manufactured by FIBERTEC™, carbon fiber, micro- or nano-sized fillers, and nanocrystalline metals and alloys, such as those manufactured by POWERMETAL TECHNOLOGIES, INC. As a non-limiting example, a suitable metal-filled resin is EC-433 High Temp Epoxy Casting System Aluminum Filled and EC-433-2 Hardener, manufactured by ADTECH PLASTIC SYSTEMS. As an alternative to resin hardening, the open cell foam may be hardened with castable ceramics, such as those manufactured under the brand name RESCOR™, including products 750 and 780.

As described in EXAMPLE 2 below, the inventors discovered that an open cell foam impregnated with an aluminum-filled epoxy resin with an apparent density of 0.31 $g/cm^3$ resulted in about 6-fold improvements in apparent modulus and ultimate stress values compared to the same open cell foam impregnated with an aluminum-filled epoxy resin with an apparent density of 0.15 $g/cm^3$ (see TABLE 2, RD3 and RD4 data). The inventors further discovered that such impregnation with an aluminum-filled epoxy resin having an apparent density of 0.31 $g/cm^3$ still achieves openness in the interstices and passages between cells to allow for permeation of a bone structure reinforcing compound, such as a bone cement compound.

In one embodiment of the present disclosure, a method for impregnating and hardening a dry, formable open cell foam with an inner core hardening agent includes the following method steps. A liquid hardening agent mixture is prepared, such as a resin, ceramic, or metal, including alloys or oxides thereof. The weight of the dry, formable open cell foam is then recorded. The dry, formable open cell foam sample is then saturated with the liquid hardening agent. Excess liquid hardening agent is then removed from the wet, saturated, formable foam sample, for example, by being squeezed through a roller system that acts like a squeegee to remove excess hardening agent. While it is important that the open cell foam be saturated with liquid hardening agent, an excess of liquid hardening agent may affect the "openness" of the cells. The weight of wet, saturated, formable open-cell foam sample is then recorded to determine whether a proper amount of saturation has occurred. For example, if the weight of the wet, saturated, formable open-cell foam is too high or low, then the weight can be adjusted by changing the distance between the roller system and repeating the squeegee process until the wet sample of foam is within a specified weight range based on dry density, such that dry density is within the range of density values for mammalian cancellous bone. The wet, saturated, formable open cell foam is then dried in a ventilated area until the hardening agent has cured. It should be appreciated that the method steps described herein for impregnating and hardening a dry, formable open cell foam with a hardening agent are exemplary in nature and not intended to be limiting.

As discussed above, a suitable hardened reticulated open cell foam, as described above, can be used as the inner core 26 of an artificial bone 20 in accordance with embodiments of the present disclosure. When in use, for example, for orthopedic repair and/or augmentation, a user can drill or cut into the bone 20 using standard orthopedic tools and cutting and drilling devices. After forming a hole in the bone 20, a bone structure reinforcing compound, such as a suitable cementitious compound used for orthopedic repair and augmentation as described above, can be injected into the inner cavity 24 of the bone 20. The bone cement permeates the inner cavity 24, and because the inner core 26 is a hardened, porous material having open passages throughout its structure, the bone cement is able to permeate the portion of the inner core 26 adjacent the hole. As a non-limiting example, orthopedic hardware (such as an orthopedic screw) can then be inserted into the hole, and the bone cement will harden around the hardware to set the hardware within the cement-reinforced inner core 26. As another non-limiting example, the bone cement can be used to augment the cancellous bone structure.

Figure 13:
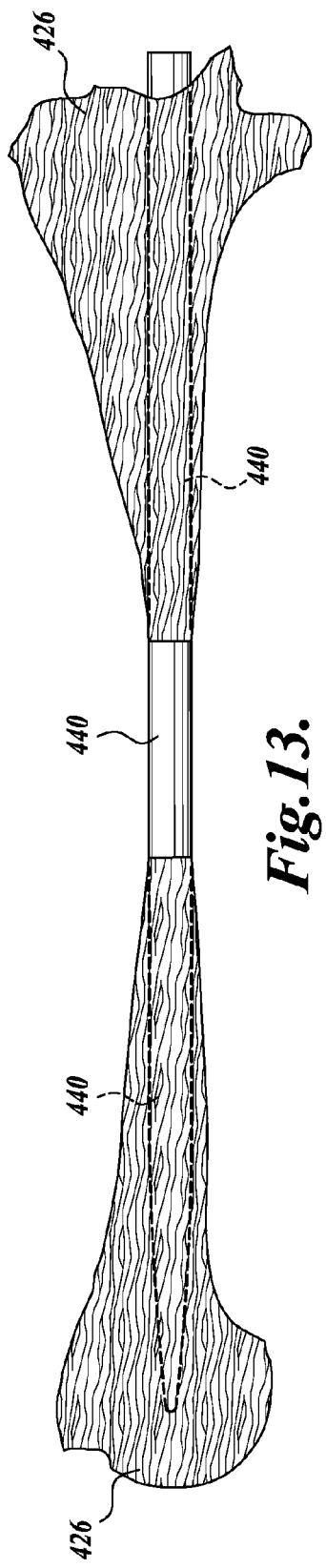
FIGS. 13-15 shows a prior art method of making an artificial bone having closed cell artificial cancellous bone.
Figure 14:
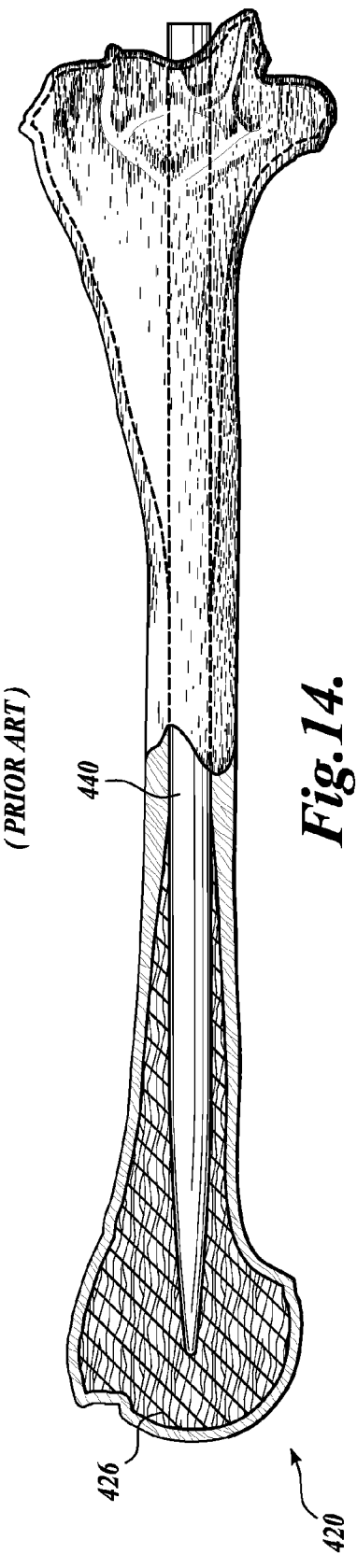
Figure 15:
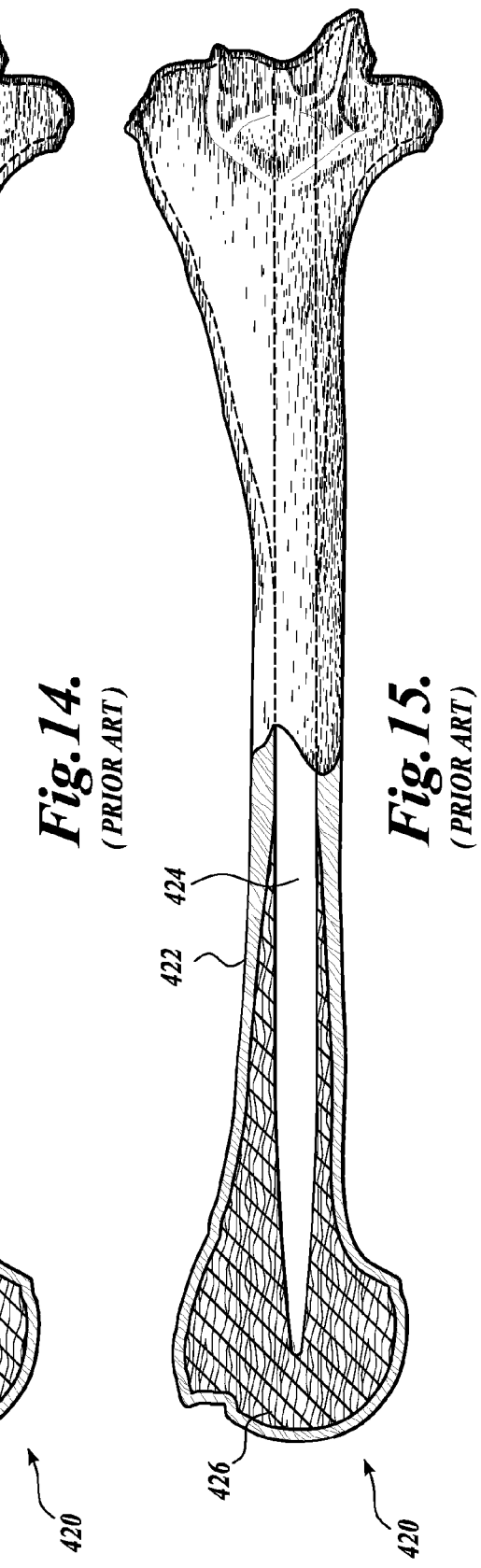

In accordance with embodiments of the present disclosure, methods of manufacturing artificial bones will now be described. Referring to FIGS. 13-15, the manufacture of artificial bones 420 having closed cell artificial cancellous bone generally includes molding, for example, by reaction injection molding, an inner core 426 of artificial cancellous bone using an inner core mold (not shown). A suitable spacer 440, shown as a pin, extending longitudinally through the inner core 426, may be used to define an inner cavity 424 (FIG. 15) in or adjacent the inner core 426. The inner core 426 may be reaction injection molded from a low density polyurethane foam material, for example, having a density in the range of about 0.08 to about 0.24 $g/cm^3$.

After the inner core 426 has been molded around the pin 440, the inner core 426 and the pin 440 are placed in a second larger mold (not shown), and an outer wall 422 is injection molded around the inner core 426 and the pin 440 (see FIG. 14). The outer wall 422 may be molded from a higher density polyurethane material than the inner core 426, for example, having a density in the range of about 0.32 to about 0.48 $g/cm^3$. After the outer wall 422 has been molded, the artificial bone 420 is removed from the mold and the pin 440 is removed from the artificial bone 420 (see FIG. 15).

If this method was used with an inner core comprising an open cell artificial cancellous bone, the polyurethane of the outer layer would permeate the interstices of the open cell artificial cancellous bone, rendering it filled and useless as an open cell structure. Because an open cell artificial cancellous bone cannot be reaction injection molded using the method described above for a closed cell bone 420, the following methods are directed to improved methods of making improved artificial bones and joints using open cell artificial cancellous bone.

A first method of manufacturing artificial bones will be described with reference to FIG. 2. The method includes forming first and second portions 30 and 32 of the outer wall 22. It should be understood that such first and second portions 30 and 32 may be formed as separate portions or as an integral outer wall 22, which is later cut into first and second portions 30 and 32. The outer wall 22, including any separate portions, may be formed by reaction injection molding or any other suitable forming method. If formed by reaction injection molding, it should be appreciated that a suitable spacer (not shown) may be inserted in the mold to define an outer wall 22 having an inner cavity 24 (see FIG. 1) during the molding process.

In the illustrated embodiment of FIG. 2, the first and second outer wall portions 30 and 32 are divided generally along the longitudinal axis of the bone 20. It should be understood, however, that the first and second outer wall portions 30 and 32 need not be divided along the longitudinal axis of the bone 20, but can be divided along any sectional portions that provide access to the inner cavity 24 of the bone 20. It should further be understood that a bone having more than first and second outer wall portions is also within the scope of this disclosure. Each of the first and second outer wall portions 30 and 32 define a portion of an inner cavity 24 such that, when the first and second outer wall portions 30 and 32 are assembled into a complete outer wall 22, the outer wall 22 defines an inner cavity 24 (see FIG. 1).

The method further includes forming an inner core 26 configured to fit within the inner cavity 24 (see FIG. 1), wherein the inner core 26 has hardness and porosity properties that are similar to mammalian bone, as described above. In accordance with the first method, the inner core 26 is hardened, for example, by resin impregnation and curing, before being formed to have characteristics and features similar to cortical bone, such that the inner core suitably fits within at least a portion of the inner cavity 24 of the bone 20. In accordance with this method, the hardened inner core 26 can be formed by being machined, cut, ground, thermoformed, molded, or otherwise formed in accordance with any other suitable forming methods.

In addition, the method includes inserting the inner core 26 within a portion of the inner cavity 24 of the first outer wall portion 30 and attaching the second outer wall portion 32 to the first outer wall portion 30 to form the outer wall 22 having an inner core 26 disposed within at least a portion of the inner cavity 24. The attachment of the first and second outer wall portions 30 and 32 may be by adhesive, heat sealing, mechanical attachment means, or any other suitable attachment mechanism. Oftentimes, a mold release formula is applied to release the first and second outer wall portions 30 and 32 from their respective molds. The inventors have found that such mold release formula may need to be removed from the first and second outer wall portions 30 and 32 before using adhesive for attachment.

A second method of manufacturing artificial bones will be described, also with reference to FIG. 2. The second method is substantially similar to the first method, except that the inner core 26 is a formable or pliable, porous material, and additional forming and hardening of the inner core 26 takes place after the inner core 26 has been fit or placed within the inner cavity 24 of the bone 20. In accordance with the second method, the porous, formable inner core 26 is formed and placed within at least a portion of the inner cavity 24. The inner core 26 is subsequently hardened (for example, by resin impregnation and curing) after being placed within the inner cavity 24. Because the inner core 26 is a porous material, as the inner core hardening agent (such as resin) is introduced into the inner cavity 24, the hardening agent readily permeates throughout the inner core 26 within the inner cavity 24. As the hardening agent cures, the inner core 26 is hardened to specific parameters in accordance with the present disclosure.

In accordance with the second method, it should be appreciated that the inner core 26 need not be formed to fit exactly within the inner cavity 24 prior to placement in the inner cavity 24, but rather is additionally formed as a result of its conforming to the shape of the inner cavity 24 into which it is placed, then hardened to maintain its form. In an alternative embodiment, the inner core 26 may be saturated with an inner core hardening agent, such as resin, outside the inner cavity 24, then inserted into the inner cavity 24 before the hardening agent has cured.

Figure 4:
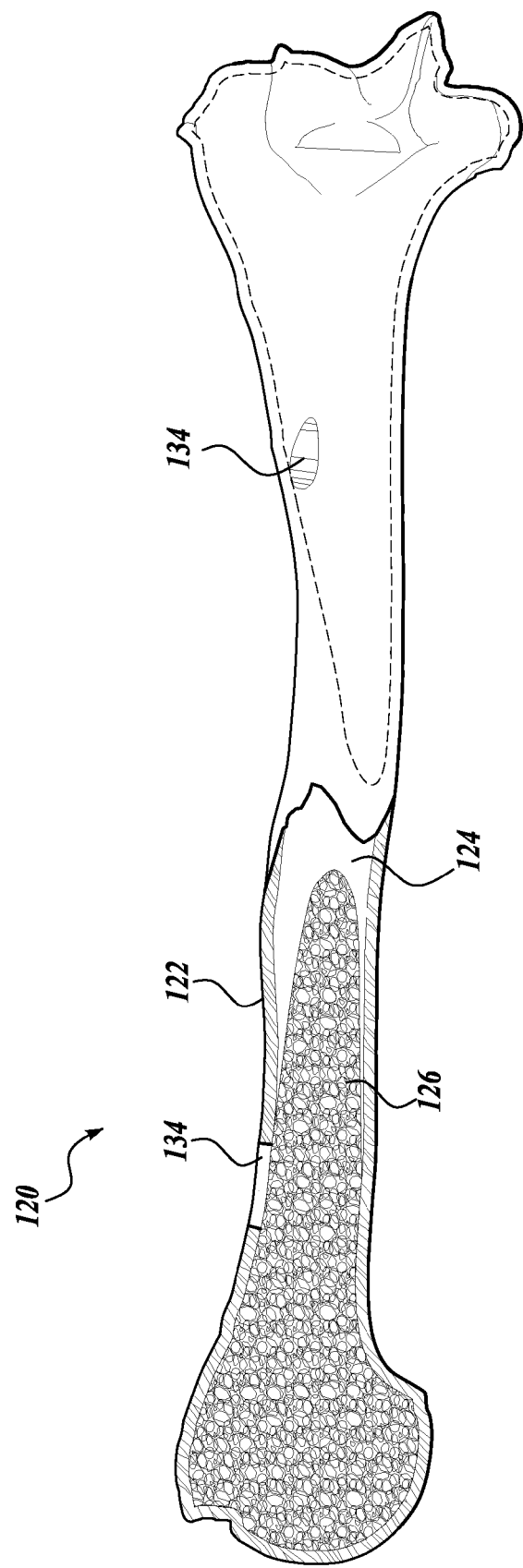
FIG. 4 is a partial cut-away view of an artificial bone of FIG. 1 formed according to other aspects of the present disclosure.

It should be appreciated that in accordance with this method, the porous, formable inner core 26 may be placed between the first and second outer wall portions 30 and 32, which are then attached to one another to form an artificial bone 20. In an alternate embodiment, as seen in FIG. 4, the inner core 126 may be inserted (or squeezed) into the inner cavity 124 through an opening 134 in the outer wall 122, i.e., instead of dividing the outer wall 122 into one or more portions, as described above. It should further be appreciated that, when inserted through an opening 134 in the outer wall 122, the inner core 126 may be saturated with an inner core hardening agent outside the inner cavity 124, then inserted into the inner cavity 124 before the hardening agent has cured, or the inner core hardening agent may be applied to the inner core 126 in the inner cavity 124 through the same opening 134. After the inserting and hardening steps, the opening 134 in the outer wall 122 can be patched with suitable patching materials.

Further in accordance with embodiments of the present disclosure, a third method of manufacturing artificial bones will now be described with reference to FIGS. 5-9. The third method is substantially similar to the first method, except that the outer wall 322 (see FIG. 9) is formed as a substantially continuous outer wall around the inner core 326 (see FIG. 5). A suitable substantially continuous outer wall 322 is substantially free of seams, for example, along the longitudinal axis of the bone 20.

Referring to FIG. 5, an inner core 326 is designed configured to fit within an inner cavity 324 of an outer wall 322 (see FIG. 9). The inner core 326 has hardness and porosity properties that are similar to mammalian bone, as described above. The inner core 326 may include a suitable spacer 344 to maintain an empty space for the inner cavity 324. In the illustrated embodiment, the spacer 344 is shown as a hollow cylinder, which may be suitably made from similar materials as the outer wall 322. It should be appreciated, however, that suitable spacers may include air-filled balloons or bladders positioned adjacent the inner core 326.

As seen in FIG. 6, the inner core 326 may include a barrier layer 342. In that regard, a barrier layer 342 is formed over the inner core 326 and the spacer 344. As a non-limiting example, a suitable barrier layer is a plastic film layer, such as a thin urethane film layer. In the illustrated embodiment of FIG. 6, the inner core 326 and spacer 344 are sealed between first and second plies of a suitable barrier layer 342. The barrier layer 342 can then be heat pressed or vacuum sealed to the inner core 26 and spacer 344 to form a barrier layer around the inner core 26. It should be appreciated that an optional adhesive may be used on the first and second plies of the barrier layer 342 to promote adhesion between the barrier layer 342 and the inner core 326. As seen in FIG. 7, excess barrier layer material can be cut away from the joining seam 346 between the first and second plies of the barrier layer 342.

In accordance with this method, first and second outer wall portions 30 and 32, as shown in FIG. 2, may be used as spacers to aid in the process of forming the barrier layer 342 around the inner core 326. In that regard, first and second outer wall portions 30 and 32 are placed in a mold, first and second plies of the barrier layer 342 are draped over the outer wall portions 30 and 32, and the inner core 326 is placed in one of the first and second outer wall portions 30 and 32. The barrier layer 342 can then be heat pressed or vacuum sealed within first and second outer wall portions 30 and 32 to form a barrier layer around the inner core 26. After the barrier layer 342 has been applied to the inner core 26, the mold can be reopened, and the first and second outer wall portions 30 and 32 can be removed from the mold.

Referring now to FIGS. 8 and 9, a substantially continuous outer wall 322, i.e., an outer wall substantially free of seams, is formed around the inner core 326 and barrier layer 342. The outer wall 322 may be configured to cover the joining seam 346 between the first and second plies of the barrier layer 342 to ensure outer wall strength along the barrier layer seam 346. In that regard, the inner core 26 having a barrier layer 342 may be returned to the mold used to form the barrier layer 342. In the absence of the first and second outer wall portions 30 and 32, which were used as spacers in the mold, the mold can be filled with an outer layer molding material, such as liquid urethane or fiberglass filled epoxy, around the inner core 326 and barrier layer 342. The molding material cures around the inner core 26 and forms a substantially continuous outer wall 22 around the inner core 26, i.e., an outer wall substantially free of seams.

Artificial bones made with a substantially continuous outer wall are significantly advantageous over artificial bones made by securing first and second outer wall portions 30 and 32 to one another, for example, with adhesive applied generally along the longitudinal axis of the bone 20. In that regard, artificial bones having a substantially continuous outer wall have a reduced failure rate, for example, when subjected to drilling or cutting in orthopedic practice and biomechanical testing, as a result of the absence of a seam along the longitudinal axis of the bone. Moreover, this method eliminates the step of removing the mold release formula which tends to prevent strong adhesive attachment between first and second outer wall portions 30 and 32.

A number of tests were performed under properly controlled conditions to investigate the characteristics and properties of the artificial bones formed in accordance with embodiments described herein. These tests results, as well as comparative data for human cancellous bone collected from several published sources, are included below in EXAMPLES 1-4. In that regard, EXAMPLE 1 includes standard morphological data for artificial cancellous bone formed in accordance with embodiments of the present disclosure and similar data for human cancellous bone obtained from human vertebrae. EXAMPLE 2 includes static compressive data for samples of artificial cancellous bone formed in accordance with embodiments of the present disclosure and similar data for human cancellous bone. EXAMPLE 3 describes results of fatigue tests performed on artificial cancellous bone formed in accordance with embodiments of the present disclosure and similar data for human cancellous bone. EXAMPLE 4 describes results from the effective strain tests performed on artificial cancellous bone formed in accordance with embodiments of the present disclosure and similar data for bovine trabecular bone, human vertebral bone, and closed cell foam.

Example 1

Standard Morphological Parameters

Standard morphological parameters of exemplary hardened reticulated open cell foam formed in accordance with embodiments of the present disclosure and data for human cancellous bone obtained from human vertebrae are shown below in TABLE 1. In TABLE 1, the following abbreviations are used: "BV/TV" is volume fraction; "BS/TV" is surface to volume ratio (in $mm^{-1}$); "Tb.N" is trabecular number (in $mm^{-1}$); "Tb.Th" is trabecular thickness (in mm); "Tb.Sp" is trabecular spacing or cell size (in mm); "MIL1,2,3" is mean intercept length (in mm); "TCI" is connectivity index (in $mm^{-1}$); "DA" is degree of anisotropy and is equal to the maximum mean intercept length (i.e., one of MIL1, MIL2, and MIL3) divided by the minimum mean intercept length (i.e., one of MIL1, MIL2, and MIL3); and a morphology characterization of "TI" is transverse isotropic.

In the following examples, samples #1521-55 and #1521-59 were both prepared using the same process, including the following method steps: (1) preparing an epoxy mixture (specific mixture described below); (2) recording the weight of the dry formable open cell foam having 14 ppi (pores per inch), manufactured by the EN MURRAY COMPANY, and sold as product PTA 14 ppi Natural having a density of 0.023 $g/cm^3$; (3) soaking the formable open cell foam sample with the epoxy mixture; (4) feeding the saturated foam sample through two aluminum rollers that act like a squeegee to remove excess epoxy; (5) recording the weight of wet formable open-cell foam sample; (6) if the weight of the wet formable open-cell foam was too high or low, then adjusting the distance between the rollers and repeating the squeegee process until the sample of foam is within a specified weight range, based on dry density; and (7) hanging the open cell foam samples in a ventilated area until the wet foam has cured.

Sample #1521-55 includes marine grade epoxy resin, manufactured by TAP®, including resin #314 blended with B-side hardener #109. Sample #1521-59 includes marine grade epoxy resin, manufactured by TAP®, including resin #314 blended with B-side hardener #109, combined with 3032 milled e-glass fiber, manufactured by FIBERTEC™, in a 1:1 ratio with the resin portion of the epoxy system.

The data on morphological parameters for human vertebral cancellous bone sample sections, included in TABLE 1 below, were obtained from the following three sources: O. Cviganovic et al., "Age- and Region-Dependent Changes in Human Lumbar Vertebral Bone," *SPINE* 29(21):2370-2375, 2004 ("Data 1"); a University of Vermont, Department of Mechanical Engineering study on micro-CT trabecular bone morphology, conducted by T. S. Keller (2004) ("Data 2"); and Parkinson et al., "Interrelationships Between Structural Parameters of Cancellous Bone Reveal Accelerated Structural Change at Low Bone Volume," *J. Bone & Mineral Res.*, Vol. 18 (2003) ("Data 3"), the disclosures of which are hereby incorporated by reference. The data in the column labeled "Data 1" were obtained from 48 samples of human cadaveric L3 vertebral cancellous bone; the data in the column labeled "Data 2" were obtained from 8 samples of human cadaveric L1-L5 vertebral cancellous bone; and the data in column of labeled "Data 3" were obtained from 280 samples of human cadaveric cancellous bone from all skeletal sites.

TABLE 1

STANDARD MORPHOLOGICAL PARAMETERS

| | Rigid Open Cell Foam | | Human Cancellous Bone | | |
|---|---|---|---|---|---|
| | #1521-55 | #1521-59 | Data 1 (Thoracic, Vertebral) | Data 2 (n = 8, Lumbar, Vertebral) | Data 3 (n = 280, all skeletal sites) |
| BV/TV | 0.079 | 0.106 | 0.095 | 0.07-0.13 | 0.036-0.344 |
| BS/BV (mm$^{-1}$) | 6.263 | 5.298 | 13.67 | 10.51-13.24 | 8.299-29.85 |
| Tb · N (mm$^{-1}$) | 0.249 | 0.280 | 0.985 | 0.48-0.74 | 0.254-1.03 |
| Tb · Th (mm) | 0.319 | 0.378 | 0.146 | 0.15-0.19 | 0.067-0.241 |
| Tb · Sp (mm) | 3.70 | 3.20 | 1.000 | 1.16-1.91 | 0.321-2.099 |
| MIL1 (mm) | 0.787 | 0.924 | 0.996 | 0.38-0.50 | — |
| MIL2 (mm) | 0.773 | 0.856 | 1.399 | 0.36-0.45 | — |
| MIL3 (mm) | 0.705 | 0.808 | 1.018 | 0.30-0.41 | — |
| TCI (mm$^{-1}$) | 0.258 | 0.157 | — | 0.08-0.26 | — |
| SMI (mm$^{-1}$) | | | 1.971 | | |
| DA | 1.12 | 1.14 | 1.37 | 1.08-1.40 | |
| Morphology | TI | TI | TI | TI | — |

The results shown above in TABLE 1 are based on micro computed tomography (micro-CT) data of hardened reticulated open cell foam samples #1521-55 and #1521-59. The data shows that the hardened reticulated open cell foam formed in accordance with embodiments of the present disclosure has some similar morphology properties to the data collected for human vertebral cancellous bone. For example, volume fraction (BV/TV), surface to volume ratio (BS/TV), and connectivity index (TCI) values for samples #1521-55 and #1521-59 are all within the ranges for the human vertebral cancellous bone Data 2.

In addition, volume fraction (BV/TV) values for samples #1521-55 and #1521-59 are both within the range for the human cancellous bone Data 3, and volume fraction (BV/TV) values for sample #1521-59 are within the ranges for human vertebral cancellous bone Data 1 and Data 2.

Figure 10C:
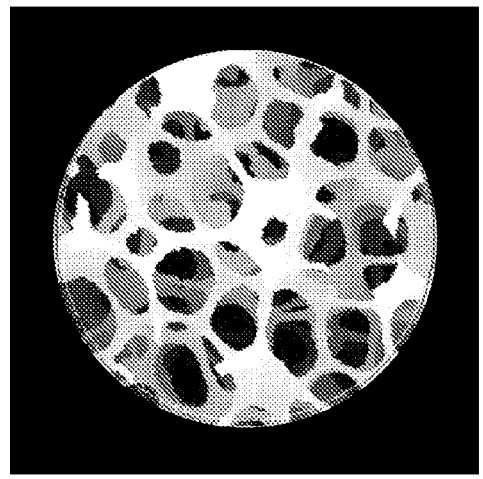
FIGS. 10B and 10C are micro computed tomography (micro-CT) renderings of artificial cancellous bone formed according to various aspects of the present disclosure.
Figure 10B:
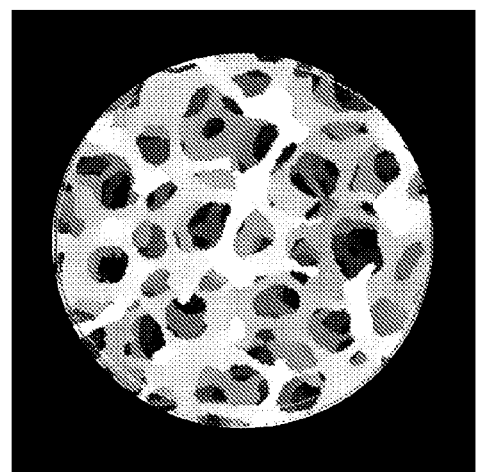
Figure 10A:
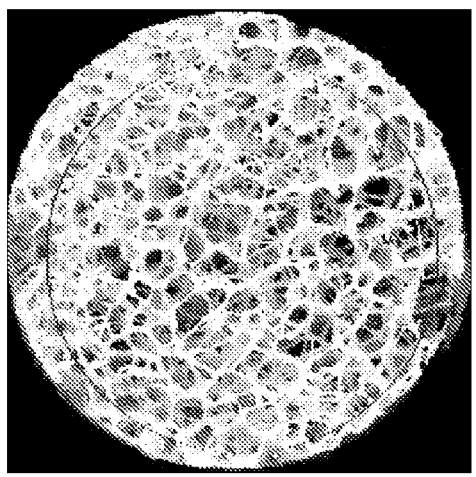
FIG. 10A is micro computed tomography (micro-CT) rendering of human vertebral cancellous bone.

In addition, the appearance of the rigid open-cell foam samples #1521-55 and #5121-59 and human cancellous bone are similar. In that regard, the characterization of the bone as transverse isotropic (TI) is the same in samples #1521-55 and #1521-59 and that of the vertebral bone data provided in Data 1 and Data 2. Moreover, both artificial and human bone have interconnected networks of rods or trabeculae, as best seen in FIGS. 10A-10C. Referring to FIG. 10A, the structure of the rigid open cell foam comprises an integrated network of thin, interconnected artificial bone trabeculae. However, when compared to the trabeculae in human cancellous bone (see FIGS. 10B and 10C), the artificial trabeculae have thicker and more widely spaced elements. In that regard, the cell size (Tb.Sp) of samples #1521-55 and #5121-59, on average, is larger (less than about 4 mm) than the cell size of typical human cancellous bone (less than about 2 mm), but the volume fractions (BV/TV) are within similar ranges.

Some of the other morphology data is outside the ranges of the vertebral bone data provided. For example, trabecular number (Tb.N) for the samples is generally lower than that of the human cancellous bone data provided; trabecular thickness (Tb.Th) is generally higher than that of the human cancellous bone data provided; trabecular spacing or cell size (Tb.Sp), mentioned above, is generally higher than that of the human cancellous bone data provided; and intercept length (MIL1,2,3) is generally higher than that of the human cancellous bone data provided. However, there is some correlation between these values for the artificial cancellous bone samples and human cancellous bone data. For example, the ratio of trabecular thickness (Tb.Th) to trabecular spacing or cell size (Tb.Sp) for sample #1521-59 is within the range for human vertebral cancellous bone Data 2 and human cancellous bone Data 3. This correlation is likely a result of the larger trabeculae cell size for artificial cancellous bone compared to that of human cancellous bone, as best seen in FIGS. 10A-10C, and the increased thickness of the artificial cancellous bone trabeculae compared to that of human cancellous bone, as a result of the resin coating. Moreover, the degree of anisotropy for the #1521-55 and #1521-59 samples are within the range of anisotropy for human vertebral cancellous bone Data 2. The degree of anisotropy is directed to the shape of the pores, with a value of 1.0 being perfectly round. The correlation between the artificial cancellous bone samples and human cancellous bone data indicates that both artificial and human cancellous bone have generally rounded pores.

Example 2

Static Compressive Properties

Static compressive properties for samples of rigid open cell foam formed in accordance with embodiments of the present disclosure and human cancellous bone are shown below in TABLE 2.

The method steps for preparing samples #1521-55 and #1521-59 are described above in EXAMPLE 1. Samples RD1, RD2, RD3, and RD4 were prepared using similar processes, including the following method steps: (1) preparing an epoxy mixture (specific mixture described below); (2) recording the weight of the dry formable open cell foam having 14 ppi (pores per inch), manufactured by the EN MURRAY COMPANY, and sold as product PTA 14 ppi Natural having a density of 0.023 g/cm$^3$; (3) soaking the formable open cell foam sample with the epoxy mixture; (4) feeding the saturated foam sample through two aluminum rollers that act like a squeegee to remove excess epoxy; (5) recording the weight of wet formable open-cell foam sample; (6) if the weight of the wet formable open-cell foam was too high or low, then adjusting the distance between the rollers and repeating the squeegee process until the sample of foam is within a specified weight range, based on dry density; and (7) hanging the open cell foam samples in a ventilated area until the wet foam has cured.

Sample RD1 uses a resin system sold under the brand names RENLAM®4017 resin and Ren® 1510 hardener as a heat resistant laminating system, manufactured by HUNTS- MAN™. The application of RD1 resin to the dry formable open cell foam results in a hardened open cell foam having an apparent density of about 0.11 g/cm³. Sample RD2 uses a resin system sold under the brand names RENLAM®4017 resin and Ren®1510 hardener as a heat resistant laminating system, manufactured by HUNTSMAN™, combined with 3032 milled e-glass fiber, manufactured by FIBERTEC™, in a 1:1 ratio with the resin portion of the system. The application of RD2 resin to the dry formable open cell foam results in a hardened open cell foam having an apparent density of about 0.18 g/cm³. Samples RD3 and RD4 used a resin system sold as EC-433 High Temp Epoxy Casting System Aluminum Filled and EC-433-2 Hardener, manufactured by ADTECH PLASTIC SYSTEMS. The application of RD3 resin to the dry formable open cell foam results in a hardened open cell foam having an apparent density of about 0.31 g/cm³, and the application of RD4 resin to the dry formable open cell foam results in a hardened open cell foam having an apparent density of about 0.15 g/cm³.

As described above, the compressive properties for human cancellous bone were compiled from mean data for 1133 compressive test samples performed on either cylindrical cores or cube specimens of human cancellous bone taken from vertebrae, femurs, and tibias from cadaver bone aged 20-100 years, using a method with uniaxial compressive loading at various strain rates. Large variations in the mechanical properties of human cancellous bone, as shown in TABLE 2 below, may be a result of differences in subject age, degeneration, bone density, and source of bone (e.g., vertebral, tibial, etc.).

The compression properties for the rigid open-cell foam samples RD1 and RD2 listed in TABLE 2 below were determined by compressive tests conducted using ASTM D1621 "Compressive Properties of Rigid Cellular Plastics" as a guide. In that regard, square blocks 76.2 mm by 76.2 mm by 40 mm were loaded to failure under displacement control (4 mm/min) using an INSTRON® 4204 load frame with a 50 kN load cell. Specimens were conditioned at 77° F. for 4 hours prior to testing. The dimensions of each specimen were measured with digital calipers and averaged over three measurements. A preload of 0.02 MPa was applied to each specimen to initiate contact with the surface and zero the displacement measurement. Load versus displacement data was collected using an INSTRON® chart recorder.

The compression properties for the rigid open-cell foam #1521-55, #1521-59, RD3, and RD4 samples listed in TABLE 2 below were determined by compressive tests conducted using a conventional mechanical test protocol used for cellular materials and cancellous bone as described in the following references: Zhu, M., Keller, T. S., Spengler, D. M., "Effects of specimen load-bearing and free surface layers on the compressive mechanical properties of cellular materials," J. Biomech. 27:57-66, 1994; and Keaveny, T. M., Borchers, R. E., Gibson, L. J., Hayes, W. C., "Trabecular bone modulus and strength can depend on specimen geometry," J. Biomech. 26:991-1000, 1993, the disclosures of which are hereby incorporated by reference. In that regard, cylindrical cores 15 mm diameter by 30 mm height were loaded to failure under displacement control (1% strain/second) using an INSTRON® 4204 load frame with a 50 kN load cell. The dimensions of each specimen were measured with digital calipers and averaged over three measurements. Specimens were potted with end caps of 2 mm polyester resin manufactured by DYNATRON®/BONDO CORP. to reinforce the load-bearing surfaces. Specimens were conditioned at 77° F. for 4 hours prior to testing. A preload of 0.02 MPa was applied to each specimen to initiate contact with the surface and zero the displacement measurement. Load versus displacement data was collected using an INSTRON® chart recorder.

The inventors have found that the two compression test methods described above achieve similar results for comparative analysis. For example, compression testing for samples #1521-55 and #1521-59 using ASTM D1621 "Compressive Properties of Rigid Cellular Plastics" as a guide resulted in the following compressive values: #1521-55, apparent density 0.09 g/cm³; apparent modulus 6.2 MPa, and ultimate stress 0.11 MPa; #1521-59, apparent density 0.12 g/cm³; apparent modulus 18.6 MPa, and ultimate stress 0.28 MPa. These results can be compared with the results in TABLE 2 below achieved by using a conventional mechanical test protocol used for cellular materials and cancellous bone, as described in the following references: Zhu, M., Keller, T. S., Spengler, D. M., "Effects of specimen load-bearing and free surface layers on the compressive mechanical properties of cellular materials," J. Biomech. 27:57-66, 1994; and Keaveny, T. M., Borchers, R. E., Gibson, L. J., Hayes, W. C., "Trabecular bone modulus and strength can depend on specimen geometry," J. Biomech. 26:991-1000, 1993.

TABLE 2

COMPRESSIVE PROPERTIES

| | Human Cancellous Bone | | Rigid Open-Cell Foam Samples | | | | | |
|---|---|---|---|---|---|---|---|---|
| | Min | Max | 1521-55 | 1521-59 | RD1 | RD2 | RD3 | RD4 |
| Apparent Density (g/cm³) | 0.09 | 0.64 | 0.08 | 0.10 | 0.11 | 0.18 | 0.31 | 0.15 |
| Apparent Modulus (MPa) | 26 | 673 | 5.2 | 12.4 | 28.9 | 72.0 | 202 | 33.8 |
| Ultimate Stress (MPa) | 0.32 | 46 | 0.09 | 0.24 | 0.38 | 0.59 | 2.6 | 0.41 |

The compression properties for the rigid open-cell foam samples listed in TABLE 2 above can be compared to the mean minimum and maximum compression properties for human cancellous bone. In that regard, the apparent density for all of the rigid open-cell foam samples fall within the minimum and maximum apparent density ranges for human cancellous bone, 0.09 to 0.64 g/cm³. However, only the apparent modulus for the RD1, RD2, RD3, and RD4 rigid open-cell foam samples fall within the minimum and maximum apparent modulus ranges for human cancellous bone, 26 to 673 MPa. Further, only the ultimate stress for RD1, RD2, RD3, and RD4 rigid open-cell foam samples fall within the minimum and maximum ultimate stress properties for human cancellous bone, 0.32 to 46 MPa.

Example 3

Modulus Degradation During Fatigue Loading

Figure 11:
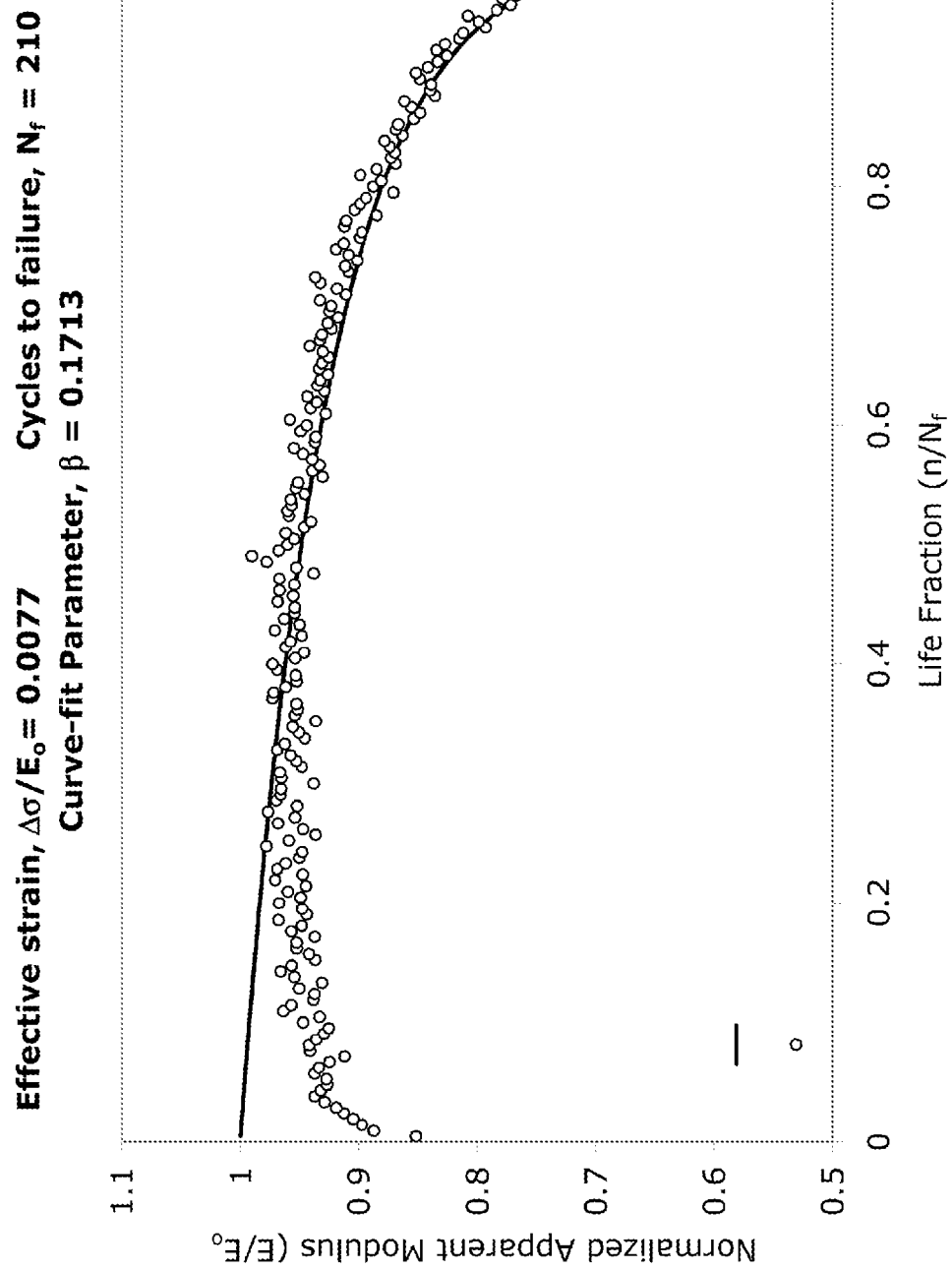
FIG. 11 is a modulus degradation curve, plotting apparent modulus versus life fraction of human cancellous bone and artificial cancellous bone formed according to various aspects of the present disclosure.

Results from the fatigue tests performed on artificial cancellous bone sample #1521-59 are plotted in FIG. 11, as compared to a curve-fit of degradation data for human cancellous bone. This data shows that artificial cancellous bone sample #1521-59, when subjected to dynamic strength tests, has similar general behavior (non-linear modulus degradation) for normalized apparent modulus of elasticity per life fraction when compared to human cancellous bone data, as published in Pattin, C. A., Caler, W. E. Carter, D. R., "Cyclic Mechanical Property Degradation During Fatigue Loading of Cortical Bone," *J. Biomechanics* 29:69-79, 1996, the disclosure of which is hereby incorporated by reference.

Example 4

S-N Curve Behavior

Figure 12:
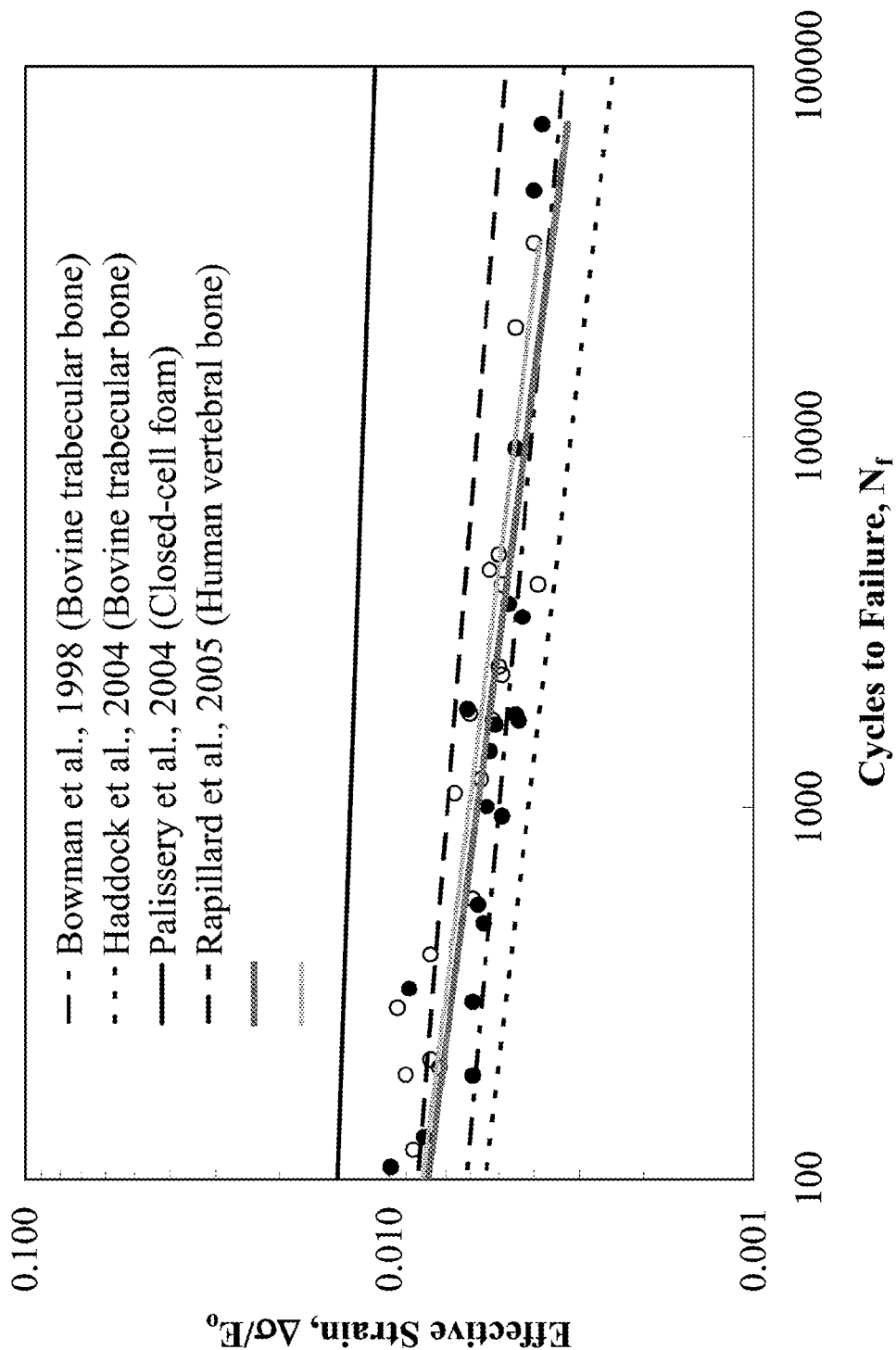
FIG. 12 is a S-N stress curve, plotting effective strain (S) versus number of cycles to failure (N) of mammalian cancellous bone, closed-cell foam, and artificial cancellous bone formed according to various aspects of the present disclosure.

Results from the effective strain tests performed on artificial cancellous bone samples #1521-59 and #1521-55 are plotted in FIG. 12 and compared to effective strain tests performed on bovine trabecular bone, human vertebral bone, and closed cell foam, showing similar S-N curve behavior. Samples #1521-59 and #1521-55 fall within the same effective strain range as human cancellous bone. Closed cell foam shows a different effective strain range than human cancellous bone. The mammalian data was published in Bowman, S., Guo, X., Cheng, D., Keaveny, T., Gibson, L., Hayes, W., McMahon, T., "Creep Contributes To the Fatigue Behavior of Bovine Trabecular Bone," *J. Biomech. Eng.* 120:647-653, 1998; Haddock, S., Oscar, Y., Praveen, M., Rosenberg, W., Keaveny, T., "Similarity in the Fatigue Behavior of Trabecular Bone Across Site and Species," *J. Biomech.* 37:181-187, 2004; Palissery, V., Taylor, M., Browne, M., "Fatigue Characterization of a Polymer Foam to Use as a Cancellous Bone Analog Material in the Assessment of Orthopaedic Devices," *J. Mat. Sci. & Mat. Med* 15:61-67, 2004; and Rapillard, L., Charlebois, M., Zysset, P. K., "Compressive Fatigue Behavior of Human Vertebral Trabecular Bone," *J. Biomechanics* [e-publication], 2005, the disclosures of which are hereby incorporated by reference.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. An artificial bone, comprising:
   (a) a substantially continuous outer wall defining an inner cavity; and
   (b) an inner core disposed within at least a portion of the inner cavity, wherein the inner core includes a porous material having stiffness within a range of stiffness properties for mammalian cancellous bone and strength within a range of strength properties for mammalian cancellous bone; and
   (c) a plastic film barrier layer disposed between the outer wall and the inner core to separate the outer wall from the porous material.

2. The artificial bone of claim 1, wherein the inner core has stiffness, measured as an apparent modulus of elasticity, within a range selected from the ranges consisting of at least 26 MPa, 26 MPa to 673 MPa, 55 MPa to 535 MPa, 26 MPa to 200 MPa, and 26 MPa to 100 MPa.

3. The artificial bone of claim 1, wherein the inner core has an apparent density within a range selected from the ranges consisting of at least 0.9 g/cm$^3$, 0.09 to 0.64 g/cm$^3$, 0.09 to 0.49 g/cm$^3$, 0.12 to 0.49 g/cm$^3$, and 0.15 to 0.49 g/cm$^3$.

4. The artificial bone of claim 1, wherein the inner core has strength measured by ultimate stress within a range selected from the ranges consisting of at least 0.32 MPa, 0.32 MPa to 46 MPa, 0.34 MPa to 12.08 MPa, 0.34 MPa to 1.0 MPa, and 0.34 MPa to 0.60 MPa.

5. The artificial bone of claim 1, wherein the inner core comprises rigid open cell foam.

6. The artificial bone of claim 5, wherein the rigid open cell foam is an open cell foam saturated with a hardening agent, selected from the group consisting of resin, ceramic, metal, and any combination thereof.

7. The artificial bone of claim 1, wherein the inner core has about 10 to about 40 pores per inch.

8. The artificial bone of claim 1, wherein the inner core has about 10 to about 20 pores per inch.

9. An artificial bone, comprising:
   (a) a substantially continuous outer wall defining an inner cavity;
   (b) an inner core disposed within at least a portion of the inner cavity, wherein the inner core comprises a porous material having a trabecular structure having an apparent modulus of elasticity of at least about 26 MPa and ultimate stress of at least about 0.32 Mpa; and
   (c) a barrier layer to separate the outer wall from the porous material.

10. The artificial bone of claim 9, wherein the inner core comprises a porous material having an apparent density of at least about 0.09 g/cm$^3$.

11. A method of making an artificial bone, comprising:
   (a) obtaining an inner core, wherein the inner core includes a porous material having a trabecular structure having stiffness within a range of stiffness properties for mammalian cancellous bone and strength within a range of strength properties for mammalian cancellous bone;
   (b) substantially covering the inner core with a barrier layer; and
   (c) molding a substantially continuous outer wall around the inner core and barrier layer.

12. The method of claim 11, wherein the outer wall includes material is selected from the group consisting of polyurethane, and fiberglass filled epoxy resin.

13. The method of claim 11, wherein the inner core comprises rigid open cell foam.

* * * * *